(12) United States Patent
Tian et al.

(10) Patent No.: US 10,478,138 B2
(45) Date of Patent: Nov. 19, 2019

(54) RT-CT INTEGRATED DEVICE

(71) Applicant: Shenyang Neusoft Medical Systems Co., Ltd., Shenyang (CN)

(72) Inventors: Shenghui Tian, Shenyang (CN); Donghui Han, Shenyang (CN); Xinzhi Tian, Shenyang (CN); Guotao Zhao, Shenyang (CN); Peng Zhou, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 412 days.

(21) Appl. No.: 15/367,211

(22) Filed: Dec. 2, 2016

(65) Prior Publication Data
US 2017/0156688 A1    Jun. 8, 2017

(30) Foreign Application Priority Data

Dec. 2, 2015 (CN) .......................... 2015 1 0873858
Dec. 2, 2015 (CN) .......................... 2015 1 0873907

(51) Int. Cl.
| | |
|---|---|
| *A61B 5/05* | (2006.01) |
| *A61B 6/00* | (2006.01) |
| *A61N 5/10* | (2006.01) |
| *A61B 6/03* | (2006.01) |
| *A61B 6/04* | (2006.01) |
| *A61B 6/10* | (2006.01) |

(52) U.S. Cl.
CPC ............ *A61B 6/4435* (2013.01); *A61B 6/032* (2013.01); *A61B 6/0407* (2013.01); *A61B 6/105* (2013.01); *A61N 5/1081* (2013.01); *A61N 2005/1094* (2013.01)

(58) Field of Classification Search
None
See application file for complete search history.

(56) References Cited

U.S. PATENT DOCUMENTS

| | | | |
|---|---|---|---|
| 7,014,361 B1* | 3/2006 | Ein-Gal | A61N 5/1049 378/197 |
| 2003/0048868 A1 | 3/2003 | Bailey et al. | |
| 2004/0024300 A1* | 2/2004 | Graf | A61N 5/1049 600/407 |
| 2006/0113482 A1 | 6/2006 | Pelizzari et al. | |

(Continued)

FOREIGN PATENT DOCUMENTS

| | | |
|---|---|---|
| CN | 101801272 A | 8/2010 |
| CN | 101879071 A | 11/2010 |

(Continued)

OTHER PUBLICATIONS

CN First Office Action dated May 31, 2019 in the corresponding CN application (application No. 201510873907.3).

(Continued)

*Primary Examiner* — Joel F Brutus
(74) *Attorney, Agent, or Firm* — Kilpatrick Townsend & Stockton, LLP

(57) ABSTRACT

An RT-CT integrated device comprising an RT system and a CT system is disclosed. The radiation-therapy centerline of the RT system and the scanning centerline of the CT system are on a same axis, and the RT system and the CT system are located at a same end of a treatment table.

16 Claims, 14 Drawing Sheets

(56) References Cited

U.S. PATENT DOCUMENTS

| | | | |
|---|---|---|---|
| 2007/0014391 A1* | 1/2007 | Mostafavi | A61B 5/064 378/63 |
| 2010/0119032 A1 | 5/2010 | Yan et al. | |
| 2012/0014501 A1 | 1/2012 | Pelc et al. | |
| 2015/0209599 A1* | 7/2015 | Schlosser | A61N 5/1049 600/427 |
| 2015/0231413 A1* | 8/2015 | Grady | A61N 5/1047 378/4 |
| 2015/0272530 A1 | 10/2015 | Umekawa et al. | |

FOREIGN PATENT DOCUMENTS

| | | |
|---|---|---|
| CN | 102188779 A | 9/2011 |
| CN | 203634188 U | 6/2014 |
| CN | 204033356 U | 12/2014 |
| CN | 104869912 A | 8/2015 |
| CN | 104939847 A | 9/2015 |
| DE | 102011080371 A1 | 2/2013 |
| WO | 9935966 A1 | 7/1999 |

OTHER PUBLICATIONS

CN First Office Action dated May 31, 2019 in the corresponding CN application (application No. 201510873858.3).

\* cited by examiner

RT-CT INTEGRATED DEVICE

BACKGROUND

The present disclosure relates to a Radiation Therapy medical linear accelerator (RT)-computed tomography scanner (CT) integrated device.

In recent decades, multi-system medical devices are constantly being developed successfully and emerged in the market. The so-called multi-system medical device may integrate two or more existing medical devices into a whole new device. For example, two existing diagnostic devices, a positron emission tomography (PET) device and a CT device, may be integrated into a new diagnostic device called "PET-CT"; two existing device, a radiation-therapy (RT) device and a diagnostic CT device, may be integrated into a new precise radiation-therapy device called "RT-CT", and so on.

Currently, the major treatments for neoplasms may be surgery, chemotherapy and radiation therapy. Among them, about 70% of the patients suffered from neoplasms need radiation therapy, and RT device is the main device used for radiation therapy. Compared with RT standalone radiation therapy, an RT-CT integrated device may perform strict quality control and quality assurance throughout the whole radiation therapy. Before and during radiation therapy of the patients, CT may be utilized to monitor neoplasms and normal organs, and to adjust radiation conditions according to variation in the positions of the organs, so that a RT device ray emitter may closely "track" the variation in the volumes and positions of the targets. And thus adaptive radiation-therapy techniques and so on may be employed to achieve precise radiation therapy in the true sense. Therefore, a RT-CT integrated device may not only significantly improve therapy effect, but also greatly reduces damage to normal tissues, thereby reducing sequela of patients to a greater extent.

NEUSOFT MEDICAL SYSTEMS CO., LTD. (NMS), founded in 1998 with its world headquarters in China, is a leading supplier of medical device, medical IT solutions, and healthcare services. NMS supplies medical device with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS's products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical device producer. As an integrated supplier with extensive experience in large medical device, NMS has been committed to the study of avoiding secondary potential harm caused by excessive X-ray irradiation to the subject during the CT scanning process.

BRIEF DESCRIPTION OF DRAWINGS

The details of one or more embodiments of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

In FIG. 1: RT device 100, CT device 200, treatment table 300.

In FIGS. 2 to 22: Rotating centerline X of RT device, rotating centerline M of CT device; RT device 1, RT device rotatable gantry 11, RT device ray emitter 12, cantilever 13, counterweight 14, RT device rotatable gantry 15, the first axial through hole 151, RT device drive part 16, RT device rotatable gantry 17, the second axial through hole 171, RT device fixing rack 18; CT device 2, CT device rotatable gantry 21, CT device ray emitter 22, CT device ray receiver 23, CT device scanning circle 24, CT device rotatable gantry 25; treatment table 3, table body 31, table plate 32, table plate support system 33; support system 4, mounting portion 41, first mounting portion 411, second mounting portion 412, support base 42, drive part 43, first drive part 431, second drive part 432, brake part 44, first brake part 441, second brake part 442, bearing 45, first bearing 451, second bearing 452, first bridge base 46, second bridge base 47; shielding system 5.

DETAILED DESCRIPTION

Figure 1:
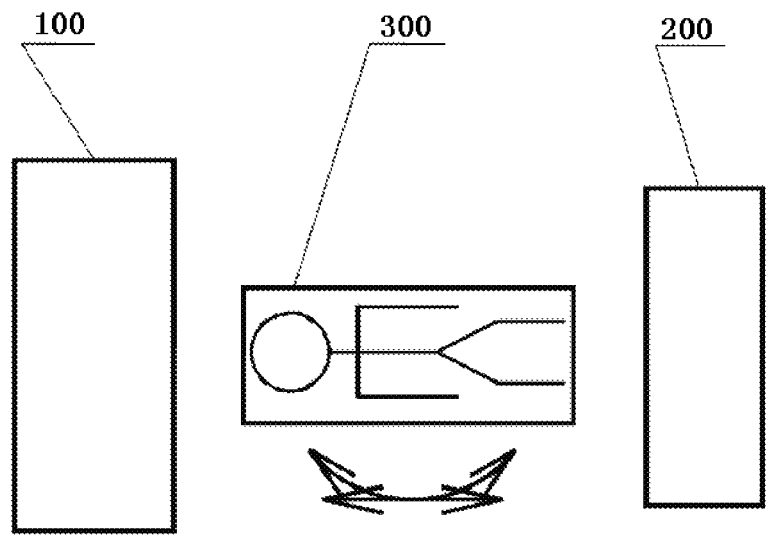
FIG. 1 is a structural schematic drawing of a set-up mode of a RT-CT integrated device.

Following is the detailed description about one kind of RT-CT integrated device combining FIG. 1. FIG. 1 is a structural schematic drawing of a set-up mode of the RT-CT integrated device.

As shown in FIG. 1, the RT-CT integrated device may have the following setting: an RT device 100 and a CT device 200 are installed in the same room. Next, a treatment table 300 shared by both devices is set, and the RT device 100 and the CT device 200 may be fixed at both ends of the treatment table 300 respectively. The treatment table 300 may move and rotate in the arrow directions shown in FIG. 1, so that a patient may be sent into the RT device 100 or the CT device 200. Specifically, when scanning with the CT device 200 is needed, the treatment table 300 may bring the patient into the scan space of the CT device 200. After the scanning is completed, the treatment table 300 may be horizontally rotated 180 degree when radiation therapy with the RT device 100 is needed, so as to turn around the head portion of the treatment table 300, thereby the treatment table 300 is directed towards the RT device 100, then the treatment table 300 is driven to bring the patient into the radiation space of the RT device 100. As can be seen, CT scan and RT radiation therapy may be accomplished, without the need of a patient's autonomic movement by using an RT-CT integrated device.

However, the use of the above RT-CT integrated device may introduce the following technical problems:

1. The distance between the RT device 100 and the CT device 200 is relatively long, therefore it is difficult to guarantee the accuracy of adjusting relative positions of the two devices, while the accuracy of relative positions of the two devices will affect the accuracy of diagnosis and radiation therapy;

2. The treatment table 300 has two motion forms, i.e. movement and rotation, as well as a relatively large number of movement dimensions, which may affect the accuracy of diagnosis and radiation therapy;

3. The RT device 100 and the CT device 200 are both relatively independent devices, and are disposed at both ends of the treatment table 300 respectively, occupying a relatively large space and thus demanding a relatively large installation room;

4. Since the distance between the RT device 100 and the CT device 200 is relatively long, it is difficult to adjust the relative positions of the two devices, and if necessary, specified tools may be employed, thus increasing the complexity of assembly and adjustment.

Accordingly, one of the objectives of the present disclosure is to provide an RT-CT integrated device, which may shorten the distance between the RT device and the CT device, and decrease the movement dimensions of the treatment table, thereby improving the accuracy of diagnosis and radiation therapy to a large extent.

Herein, combining the drawings, the RT-CT integrated device according to an example of the present disclosure will be described in detail.

The terms "up" and "down", as described herein, take a normal operating state of the RT-CT integrated device as reference. That is, when the RT-CT integrated device is in normal use, "down" is the direction close to the ground, whereas "up" is the direction away from the ground.

The term "axial direction", as described herein, may be referred to as an extending direction of the central axis of the RT-CT integrated device. Specifically, rotating centerline X of the RT device is the central axis of the RT device, and rotating centerline M of the CT device is the central axis of the CT device, thus "axial direction" refers to the extending directions of the rotation centerline X of the RT device and the rotating centerline M of the CT device.

For convenience of description, a fore-and-aft direction may also be defined in this context. The term "forward and backward", as described herein, take the treatment table as reference, and "forward" may be referred to as the pointing direction of the head portion of the treatment table along the axial direction. That is, if the entire RT-CT integrated device is located in front of the treatment table, a device close to the treatment table is at backward, whereas a device far away from the treatment table is at forward.

The terms "first", "second" and the like, as described herein, are only intended to distinguish between two or more parts with the same or similar structure, but not imply a particular order.

As shown in FIGS. 2-4 and FIG. 15, the RT-CT integrated device according to an example of the present disclosure (herein simply referred to as integrated device) may comprise RT device 1 and CT device 2. In the integrated device, the RT device 1 and the CT device 2 may be disposed at the same end of the treatment table 3, and the rotation centerline X of the RT device 1 and the rotation centerline M of the CT device 2 may be on the same axis, in other words, the RT device 1 and the CT device 2 may be disposed coaxially.

Specifically, the RT device 1 and the CT device 2 may be arranged at the same end of the treatment table 3 in the axial direction. Theoretically, on condition that the rays from the RT device 1 and from the CT device 2 do not interfere with each other, the RT device 1 and the CT device 2 may also be arranged in a nested structure. That is, one of the two devices is sleeve-fitted on the external of the other device. The present disclosure will only describe a set-up mode in axial arrangement of the RT device 1 and the CT device 2 in detail.

Figure 2:
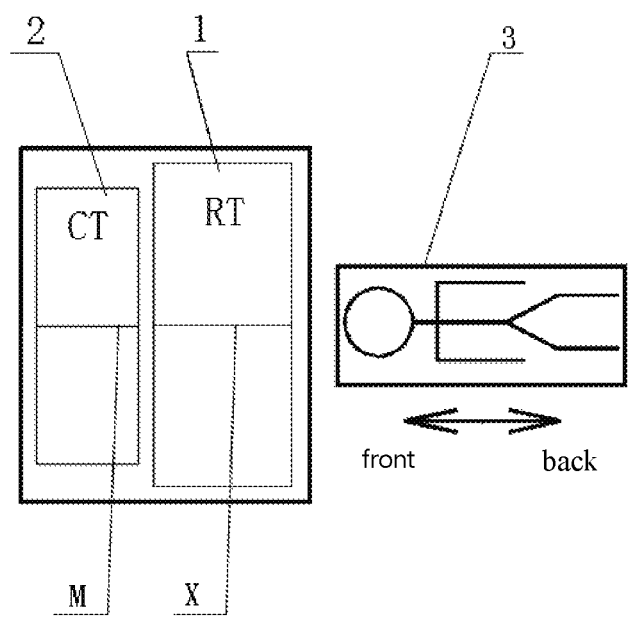
FIG. 2 is a structural schematic drawing of an RT-CT integrated device with integrated set-up mode, according to an example of the present disclosure.
Figure 3:
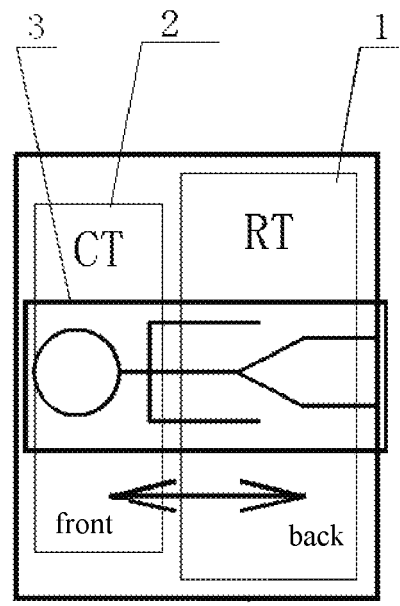
FIG. 3 is a structural schematic drawing of the RT-CT integrated device as shown in FIG. 2 in the first operating condition.
Figure 4:
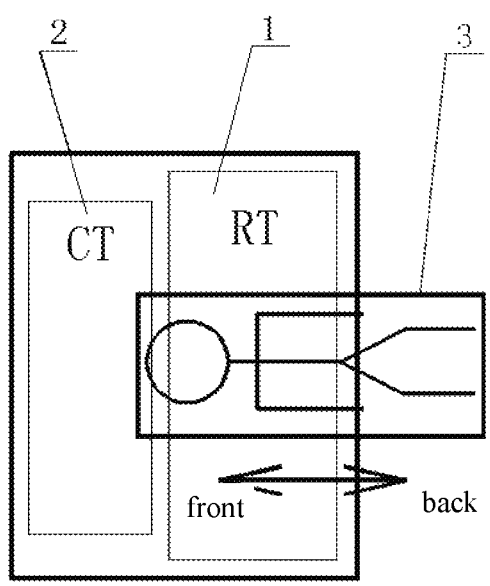
FIG. 4 is a structural schematic drawing of the RT-CT integrated device as shown in FIG. 2 in the second operating condition.
Figure 5:
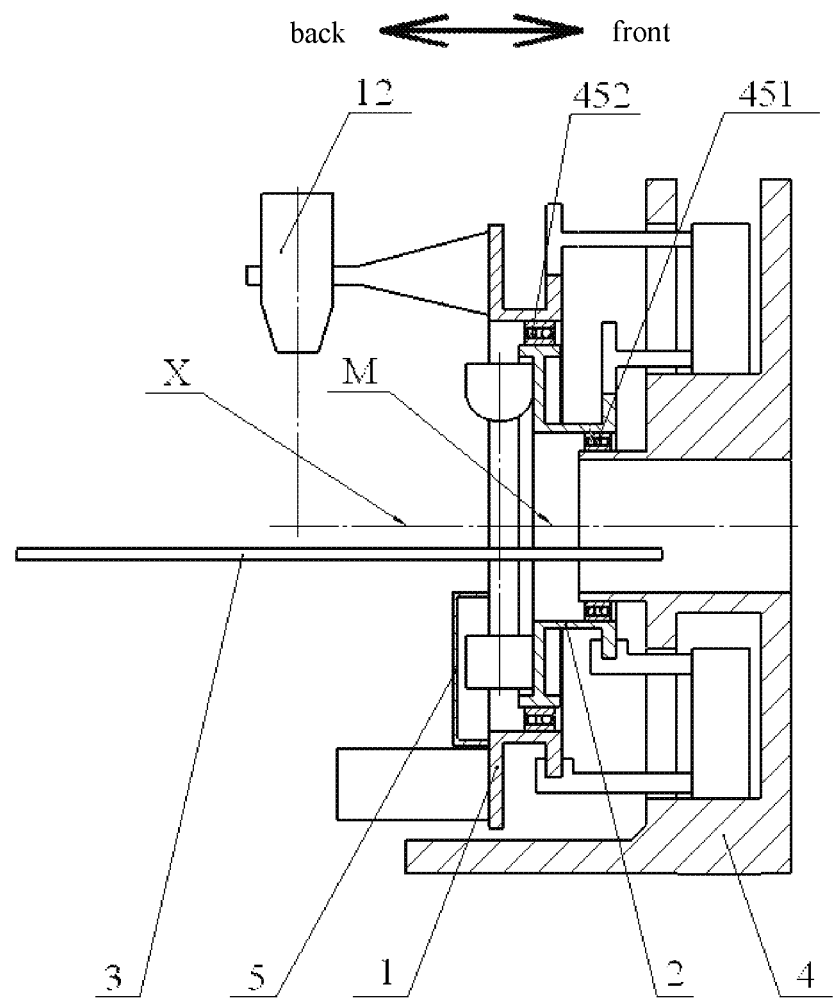
FIG. 5 is a cross-sectional structural schematic drawing of the RT-CT integrated device as shown in FIG. 2 in Embodiment 1.

As shown in FIGS. 2 to 4, in one set-up mode, the RT device 1 and the CT device 2 may be integrated, combined to form an integrated device. That is, the CT device 2 and the RT device 1 adopt an integrated structure. As shown in FIG. 5, a unified support system 4 may be set, and then the radiation-therapy related devices and CT-diagnosis related devices are integrated into the support system 4, and constitute the RT device 1 and the CT device 2 respectively.

Figure 15:
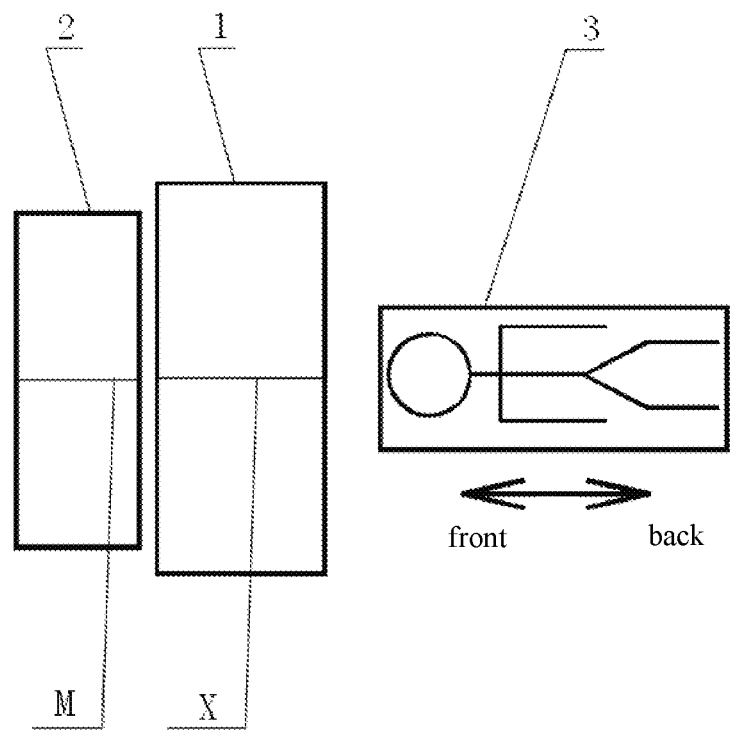
FIG. 15 is a structural schematic drawing of an RT-CT integrated device with separated set-up mode, according to an RT-CT integrated device of another example of the present disclosure.

As shown in FIG. 15, in another set-up mode, the RT device 1 and the CT device 2 may be relatively independent without connection. Therefore, the integrated device now presents a separated structure. The RT device 1 and the CT device 2 may be arranged at the same end of the treatment table 3 and spaced along the fore-and-aft direction, and the two devices may have a predetermined axial spacing therebetween.

In the integrated device in accordance with the present disclosure, the RT device 1 and the CT device 2 are arranged sequentially along the axial direction and at the same end of the treatment table 3 whether it is an integrated device formed by combination or a relatively independent separated structure. During a switching process between a diagnosis mode and a therapy mode, the treatment table 3 only needs to move along the forward and backward direction, without rotation in the horizontal plane. As shown in FIGS. 2 to 4 and FIG. 15, the integrated device of the present disclosure enables the switching between diagnosis and treatment with only back-and-forth movement of the treatment table 3 along the axial direction. Since the forth-and-back movement is a linear motion, and the accuracy of linear motion is easy to control, the movement accuracy is higher when the treatment table 3 only moves in the forward and backward dimension. Thus, the treatment table 3 can carry a patient from a diagnosis position to a therapy position horizontally more accurately, thereby reducing the influence of the treatment table 3 on diagnosis and therapy, and obtaining a higher level of matching accuracy between the diagnosis position and the therapy position, as well as reducing inaccuracy between the therapy position and an actual position of neoplasms. Therefore, therapy effect can be improved and the possibility of damage to healthy cells is reduced.

Further, the RT device 1 and the CT device 2 of the integrated device are arranged sequentially along the axial direction of the same end of the treatment table 3, and there is no need for the treatment table 3 to rotate in the horizontal plane with such arrangement, thus avoiding the feeling of vertigo and fear during rotation, improving comfort level during the diagnosis and therapy process for patients.

Moreover, since the RT device 1 and the CT device 2 are arranged at the same end of the treatment table 3, such arrangement can narrow the spacing between the RT device 1 and the CT device 2 as much as possible, compared with the structural form that the RT device 1 and the CT device 2 are disposed at both ends of the treatment table 3 respectively. As the spacing between the two devices is narrowed, the coaxiality of the two devices can be guaranteed; meanwhile the difficulty of controlling the coaxiality will be greatly reduced. Moreover, as the spacing between the RT device 1 and the CT device 2 is narrowed, installation space for the entire integrated device can be reduced, and the limitation on using the integrated device can be reduced, thus is more advantageous to promote the application of the integrated devices.

More specifically, FIGS. 2 to 4 and FIG. 15 illustrate, by way of example, a case in which the CT device 2 is at backward and the RT device 1 is at forward. However, one skilled in the art should appreciate that the RT device 1 may be at forward and the CT device 2 is at backward. In other words, the forward and backward order of the arrangement of the RT device 1 and the CT device 2 may be exchanged. When the fore-and-aft order of the arrangement is exchanged, it only needs to replace the corresponding connection structure, and in the present disclosure, only one arrangement will be described by way of example in detail.

As shown in FIG. 3 and FIG. 4, when diagnosis is needed, the treatment table 3 may be driven to move forward along the arrow direction shown in FIG. 3, to carry the patient into the CT device 2. When treatment is needed, the treatment table 3 may be driven to move backward along the arrow direction shown in FIG. 4, to carry and transfer the patient into the RT device 1 from the CT device 2, so that radiation therapy may be performed to the diseased positions according to the scan result of the CT device 2. The steps described above are applicable to the separated structure shown in FIG. 15 similarly.

Next, the integrated device with integrated structure shown in FIGS. 2-4 will be described in detail by reference of FIGS. 5 to 14. For the integrated structure, three examples are provided below for illustration.

Embodiment 1

Figure 6:
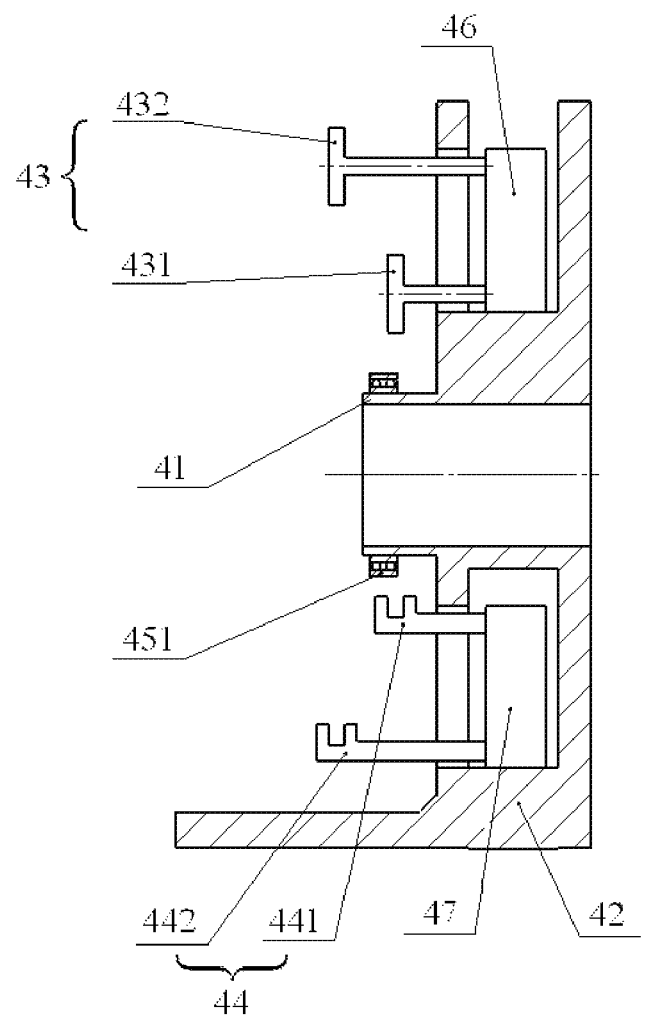
FIG. 6 is a cross-sectional structural schematic drawing of the support system in the RT-CT integrated device as shown in FIG. 5.
Figure 7:
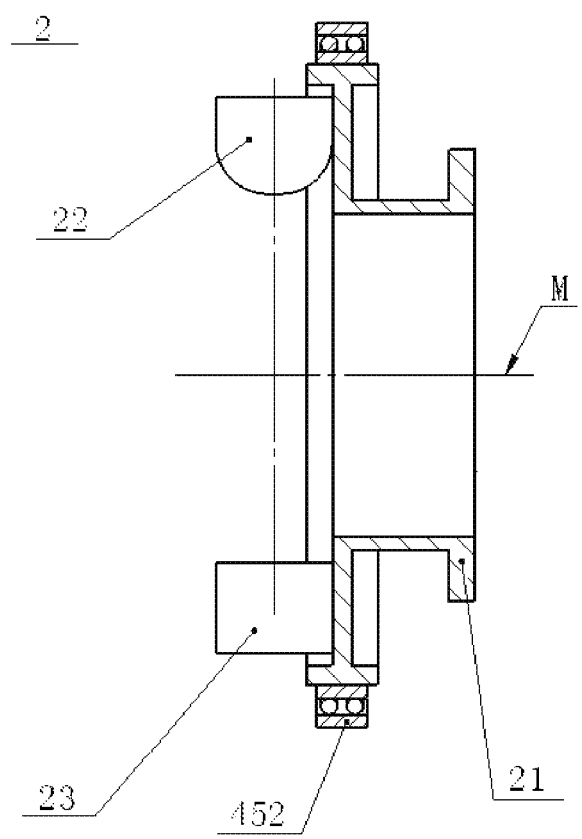
FIG. 7 is a cross-sectional structural schematic drawing of the CT system in the RT-CT integrated device as shown in FIG. 5.
Figure 8:
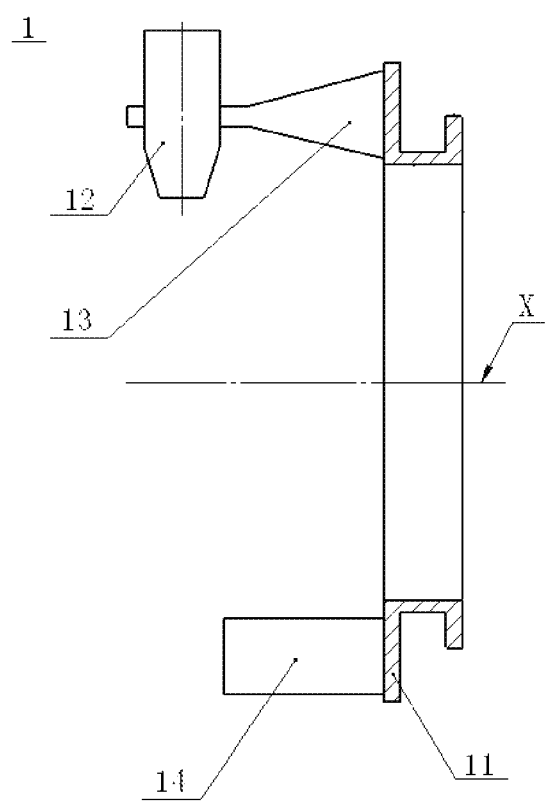
FIG. 8 is a cross-sectional structural schematic drawing of the RT system in the RT-CT integrated device as shown in FIG. 5.

As shown in FIGS. 5 to 8, the integrated device may comprise an RT device 1 and a CT device 2 which are both set on the same support system 4. As shown in FIG. 6, the support system 4 may comprise a support base 42 that may be equipped with mounting portion 41. As shown in FIG. 7, the CT device 2 may comprise CT device rotatable gantry 21, CT device ray emitter 22 and CT device ray receiver 23. As shown in FIG. 8, the RT device 1 may comprise RT device rotatable gantry 11 and RT device ray emitter 12. The CT device ray emitter 22 and the CT device ray receiver 23 may both be set on the CT device rotatable gantry 21, and the RT device ray emitter 12 may be set on the RT device rotatable gantry 11. The RT device rotatable gantry 11 and the CT device rotatable gantry 21 are both socket-jointed on the support base 42 of mounting portion 41. The RT device rotatable gantry 11, the CT device rotatable gantry 21 and the mounting portion 41 may be disposed coaxially. The CT device rotatable gantry 21 and RT device rotatable gantry 11 may be fixed in axial direction as well as in radial direction and rotational connection along circumferential direction. In addition, both the RT device rotatable gantry 11 and the CT device rotatable gantry 21 may be set as hollow columnar structure and form a hollow annular rotating disc structure.

The RT device rotatable gantry 11 and the CT device rotatable gantry 21 may be socket-jointed with the mounting portion 41 in a variety of ways. For example, they may be socket-jointed directly with the mounting portion 41. As another example, one of them may be socket-jointed with the other, and then the other may be socket-jointed with the mounting portion 41. In this embodiment, by way of example, the example that the RT device rotatable gantry 11 is socket-jointed on the CT device rotatable gantry 21 will be described.

As shown in FIGS. 5-8, the RT device rotatable gantry 11, the CT device rotatable gantry 21 and the mounting portion 41 may be sequentially socket-jointed along the axial direction. That is: the RT device rotatable gantry 11 may be socket-jointed with its back-end to the front-end of the CT device rotatable gantry 21, and the CT device rotating gantry 21 may be socket-jointed with its back-end to the front-end of the mounting portion 41, then the mounting portion 41 may extend along the axial direction and set its back-end fixed on the support base 42. Each joint position may be fixed in axial direction as well as in radial direction and rotational connection along circumferential direction.

As shown in FIG. 6, the support base 42 may be set substantially in L-shape, with the transversal portion of the L-shape supported on the ground and the vertical portion of the L-shape extending upward. Thus, the mounting portion 41 may be set at the vertical portion of the L-shape, and may extend substantially along the horizontal direction, particularly along the same direction of the transversal portion of the L-shape. Then, the CT device rotatable gantry 21 and the RT device rotatable gantry 11 may be set as hollow columnar rotatable gantries, and sequentially socket-jointed with the mounting portion 41. By providing adapting parts such as bearings and so on, an integrated device which is only rotatable along circumferential direction may be formed after socket-joint.

As shown in FIG. 6, in the support system 4, the support base 42 may be used to bear the load of the entire integrated device, and thus may be directly placed or fixed on the ground. The mounting portion 41 may be a solid columnar structure, also may be a hollow columnar structure, and particularly may be set as a columnar structure with a through hole extending in the axial direction. As mentioned above, while the support base 42 is set substantially in an L-shaped form, the mounting portion 41 may be set at the vertical portion of the L-shape, and may extend along the horizontal direction from the inner end surface of the vertical portion (towards the end surface of the transversal portion), with the transversal direction now being the axial direction.

Specifically, the mounting portion 41 may be socket-jointed with its front-end to the vertical portion of the support base 42 and its back-end extending towards the treatment table 3. As shown in FIG. 6, a first bearing 451 may be set at the back-end of the mounting portion 41, so the inner surface of the first bearing 451 coordinates with the mounting portion 41, and the outer surface of the first bearing 451 coordinates with the inner surface of the CT device rotatable gantry 21. The outer surface of the mounting portion 41, which coordinates with the inner surface of the first bearing 451, may be formed through machining, and form an outside axle journal to coordinate with the inner surface of the first bearing 451, so that the centerline of the first bearing 451 and the centerline of the mounting portion 41 are maintained in good coaxiality with the centerline of the entire integrated device, thereby providing a good foundation for assembly of the CT device rotatable gantry 21.

The support system 4 may further comprise drive part 43, and may drive the RT device rotatable gantry 11 and the CT device rotatable gantry 21 to rotate along circumferential direction through drive part 43. The drive part 43 may particularly comprise a driving wheel, and a driven wheel matching with the driving wheel may be set on the RT device rotatable gantry 11 and the CT device rotatable gantry 21, then driving or not of the RT device rotatable gantry 11 and the CT device rotatable gantry 21 may be realized through engagement and disengagement of the wheels. Further, the driven object may be changed by changing the driven wheel to be engaged with the driving wheel.

As shown by the implementation illustrated in FIG. 6, the drive part 43 may be set in two parts. That is, the drive part 43 may comprise a first drive part 431 and a second drive part 432 connected with a first bridge base 46, with both being set in form of driving wheels, and, of course, also may be a drive screw, a drive disc or a drive shaft or other structures. The first drive part 431 may be connected with the CT device rotatable gantry 21, to drive the CT device rotatable gantry 21 to rotate along circumferential direction. The second drive part 432 may be connected to the RT device rotatable gantry 11, to drive the RT device rotatable gantry 11 to rotate along circumferential direction. When a different drive structure is employed, the RT device rotatable gantry 11 and the CT device rotatable gantry 21 will also provided with corresponding coordinating structure to implement power transmission. Taking a driving wheel as an example, the first drive part 431 and the second drive part 432 may be both in connection with a power source, and output power through an axially-extending coupling shaft to a power-output part such as a transmission gear, while each power-output part may be set at a corresponding position to a respective rotatable gantry, thus achieving driving.

It is also possible to set a self-locking function to the drive part 43, so as to achieve such an effect that one of the RT device rotatable gantry 11 and the CT device rotatable gantry 21 is braked whereas the other may rotate relatively to the braked one. For example, the first drive part 431 may be a drive gear, and an engaging tooth which can engage with the first drive part 431 may be set at the outer circumference of the CT device rotatable gantry 21. When the first drive part 431 does not output driving force, the freedom degrees of the first drive part 431 in all directions are restricted by locking it, so that the CT device rotatable gantry 21 can be locked, achieving brake of the CT device rotatable gantry 21. Similarly, the second drive part 432 may also have the self-locking function, so as to achieve the brake of the RT device rotatable gantry 11. That is to say, braking function may be integrated on the drive part 43, without the need of setting a brake part 44 separately, so that separate driving and separate braking of the RT device rotatable gantry 11 and the CT device rotatable gantry 21 can also be achieved.

The support system 4 in the application may also provided with a brake part 44 separately for braking of the RT device rotatable gantry 11 and the CT device rotatable gantry 21. According to an example, the brake part 44 may be a part which brakes the RT device rotatable gantry 11 or the CT device rotatable gantry 21 selectively. According to another example, the RT device rotatable gantry 11 and the CT device rotatable gantry 21 may also provided with a corresponding brake part 44 separately. As shown in FIG. 6, the brake part 44 may comprise a first brake part 441 for braking the rotatable gantry 21 of CT device and a second brake part 442 for braking the RT device rotatable gantry 11.

The brake part 44 may be a brake structure in any forms. For example, the brake part may be a brake pad achieving braking by friction, or may be a brake wheel by frictional contact, and also may be a stopping part.

Meanwhile, a corresponding control unit may be set on support system 4, such as a drive control unit in signal connection with the drive part 43, a brake control unit in signal connection with the brake part 44, etc.

When the drive part 43 comprises the first drive part 431 and the second drive part 432, the first drive part 431 and the second drive part 432 may be both connected with the drive control unit. Under such condition, when a drive command is received, the first drive part 431 or the second drive part 432 may conduct driving of the CT device rotatable gantry 21 or the RT device rotatable gantry 11, according to the requirement of the command. When the drive command is not received by the first drive part 431 or the second drive part 432, the rotation of the CT device rotatable gantry 21 or the RT device rotatable gantry 11 may be prohibited, so as to achieve the above-mentioned lock-brake function.

When a brake control unit is set, a brake command may be sent to the brake part 44 by the brake control unit, so as to control braking of the CT device rotatable gantry 21 or the RT device rotatable gantry 11. Take one case as an example wherein the brake part 44 comprises the first brake part 441 and the second brake part 442, both of the brake parts may be in signal connection with the brake control unit. In this case, when the first brake part 441 or the second brake part 442 receives a brake command, they may restrain rotation of the CT device rotatable gantry 21 or the RT device rotatable gantry 11, according to the request of the command, in order to achieve brake of the corresponding rotatable gantry. When the first brake part 441 or the second brake part 442 does not receive a brake command, the brake of the CT device rotatable gantry 21 or the RT device rotatable gantry 11 may be relieved.

The brake control unit and the drive control unit may also be in signal connection, for coordination of the brake signal and the drive signal, thus avoiding conflict of control command. Moreover, the content of the drive command and the brake command may be defined as required. In the embodiments mentioned above, as an example, the following case is illustrated, wherein take a drive command to perform a driving operation while take a brake command to perform a braking operation. It is possible for one skilled in the art to adjust a drive command as not to perform a driving operation, and also adjust a brake command as not to perform a braking operation and so on. Specifically, the adjustment may be made according to the normal operations of the CT device rotatable gantry 21 and the RT device rotatable gantry 11.

The term "signal connection" as described herein, may be referred to as a type of connection to achieve signal transmission with a wired or wireless way.

As shown in FIG. 7, the CT device rotatable gantry 21 may be set in hollow ring-shape, and its front-end at inner surface may be set as a structure that coordinates with the above first bearing 451. Outer surface of the CT device rotatable gantry 21 may be set as the corresponding form that coordinates with the first drive part 431, more specifically may be any position of outer surface, such as front-end, back-end or the portion between front-end and back-end.

The second bearing 452 may be assembled at outer surface of back-end of the CT device rotatable gantry 21 for connecting the RT device rotatable gantry 11. Where, the part of the CT device rotatable gantry 21 assembled with the second bearing 452 may be processed through machining to form an outside axle journal coordinated with the second bearing 452, further ensuring the coaxiality between the CT device rotatable gantry 21 and the second bearing 452. Similarly, the part of the CT device rotatable gantry 21 assembled with the first bearing 451 may be processed through machining to form an inner axial hole coordinated with the first bearing 451, further ensuring the coaxiality between the CT device rotatable gantry 21 and the first bearing 451.

As shown in FIG. 7, in CT device 2 of the present application, the CT device ray emitter 22 and CT device ray receiver 23 may be set on both sides of radial direction on the CT device rotatable gantry 21, which may ensure the ray emitted by the CT device ray emitter 22 received by CT device ray receiver 23. Furthermore, during the rotation of the CT device rotatable gantry 21, the CT device ray emitter 22 and CT device ray receiver 23 will follow the rotation; when the CT device ray emitter 22 and CT device ray receiver 23 are set on both sides of radial direction, degree of balance of the CT device rotatable gantry 21 may be improved, further improving stability of the rotation. When the CT device rotatable gantry 21 is socket-jointed on mounting portion 41, the CT device ray emitter 22 and CT device ray receiver 23 may be in the up and down direction. For example, as shown in FIG. 7, the CT device ray emitter 22 is at the top and CT device ray receiver 23 at the bottom.

The CT device ray emitter 22 and CT device ray receiver 23 may also be set on back-end of the CT device rotatable gantry 21 and be close to the direction of treatment table 3, so as to shorten the displacement distance when treatment table 3 stretching into the scanning space and improve support reliability to the patients by treatment table 3. Of course, one skilled in the art may adjust assembling positions of the CT device ray emitter 22 and CT device ray receiver 23, which also may be at front-end of the CT device rotatable gantry 21 or any position on axial direction of the CT device rotatable gantry 21 without limited to the back-end thereof.

The CT device ray emitter 22 and CT device ray receiver 23 may be assembled in pairs. For example, multiple pairs of the CT device ray emitter 22 and CT device ray receiver 23 may be set, and pairs of the CT device ray emitter 22 and CT device ray receiver 23 may be set on both sides of radial direction for a full scanning on patient.

As shown in FIG. 8, in the RT device 1 of the present application, the RT device ray emitter 12 may be on top of the RT device rotatable gantry 11, and it may also be set at back-end of the RT device rotatable gantry 11, that is, it is close to the end of treatment table 3 and away from the CT device rotatable gantry 21. At this moment, on the one hand, the RT device ray emitter 12 may have more space for assembling, increasing convenience for assembling; on the other hand, the RT device ray emitter 12 may be kept away from the CT device ray emitter 22 and CT device ray receiver 23 as far as possible, so as to avoid interference with CT device 2 and to decrease the damage on CT device 2 attributing to high energy ray emitted from the ray emitter 12.

More specifically, a cantilever 13 may be set on RT device 1 and the cantilever 13 may stretch approximately along axial direction or stretch from front to back. Front-end of cantilever 13 constitutes its root portion, and the back-end constitutes its head portion, then root portion of cantilever 13 may be fixed to RT device rotatable gantry 11, after that, as shown in FIG. 8, the RT device ray emitter 12 may be assembled on the head portion of cantilever 13.

The ray emitted from the RT device ray emitter 12 is MV-level high energy ray while the ray emitted from the CT device ray emitter 22 is KV-level ray. Thus the ray emitted from the RT device ray emitter 12 may damage CT device 2. Through the cantilever 13 mentioned above, axial distance between RT device ray emitter 12 and CT device 2 may be increased, and then, certain safe distance may exist between RT device ray emitter 12 and CT device 2, which may prevent the damage on CT device 2 attributing to ray emitted from the ray emitter 12, especially the damage on CT device ray receiver 23.

One skilled in the art may adjust the length of cantilever 13 as needed. For example, the length of cantilever 13 may be increased as needed, so as to extend the distance from RT device ray emitter 12 to CT device 2.

As shown in FIG. 5, one skilled in the art may also set a shielding system 5, specifically, the shielding system 5 may be set on back-end of CT device ray receiver 23, so as to shield the ray emitted from the RT device ray emitter 12 that may be received by CT device ray receiver 23. The shielding system 5 may be in structural form of shield plate, and etc. The position of shielding system 5 is also not limited to back-end of the CT device ray emitter 22. Specifically, the position of shielding system 5 may be at any position on the full ray transmission path from the RT device ray emitter 12 to CT device ray receiver 23.

As shown in FIG. 8, RT device 1 may also comprise a counterweight 14. The counterweight 14 is not within the same circumference as the RT device ray emitter 12. Specifically, counterweight 14 may be on the other end of radial line of the RT device ray emitter 12 to make the RT device rotatable gantry 11 rotate evenly and to improve rotational stability of the RT device rotatable gantry 11.

To obtain assembly of the RT device rotatable gantry 11, the front-end of the RT device rotatable gantry 11 may be socket-jointed on the second bearing 452 mentioned above, specifically, it may be socket-jointed on the outer surface of the second bearing 452. At this moment, inner end surface of the RT device rotatable gantry 11 may be processed through machining to form an inner axial hole coordinated with outer surface of the second bearing 452, so as to ensure the coaxiality between the RT device rotatable gantry 11 and the second bearing 452. Finally, the RT device rotatable gantry 11, RT device rotatable gantry 21 and mounting portion 41 have higher coaxiality, and precision of diagnosis and treatment is improved.

In addition, in the present embodiment, the socket-joint is obtained through the first bearing 451 and the second bearing 452, thus can ensure the reliability of positioning of axial direction and radial direction at the socket-joint position and also provide sufficient circumferential rotational freedom to the two mutual socket-jointed parts. In this way, integrated device not only is simple in structure, but also possesses higher operational reliability and convenience. Of course, one skilled in the art may also adopt other connecting manner to obtain circumferential rotation besides bearing fit, which will not be mentioned here.

Furthermore, the axial hole and axle journal coordinated with the first bearing 451 and the second bearing 452 may all be processed through machining, so as to ensure the coaxial setting of the first bearing 451, the second bearing 452 and the RT device rotatable gantry 11, the CT device rotatable gantry 21 as well as the mounting portion 41.

In the present embodiment, as an example, "socket-jointing the CT device rotatable gantry 21 outside the mounting portion 41, socket-jointing the RT device rotatable gantry 11 outside the CT device rotatable gantry 21" is illustrated. However, it is only one detailed socket-joint manner, and the internal and external relationships at each socket-joint position can be interchanged.

Embodiment 2

As shown in FIGS. 9 to 12, as mentioned above in Embodiment 1, the RT device rotatable gantry 11 and the CT device rotatable gantry 21 can also be directly socket-jointed with mounting portion 41. Taking Embodiment 1 as an example, in the present embodiment the RT device rotatable gantry 11 and the CT device rotatable gantry 21 are socket-jointed on the both ends of support base 42 respectively.

Figure 9:
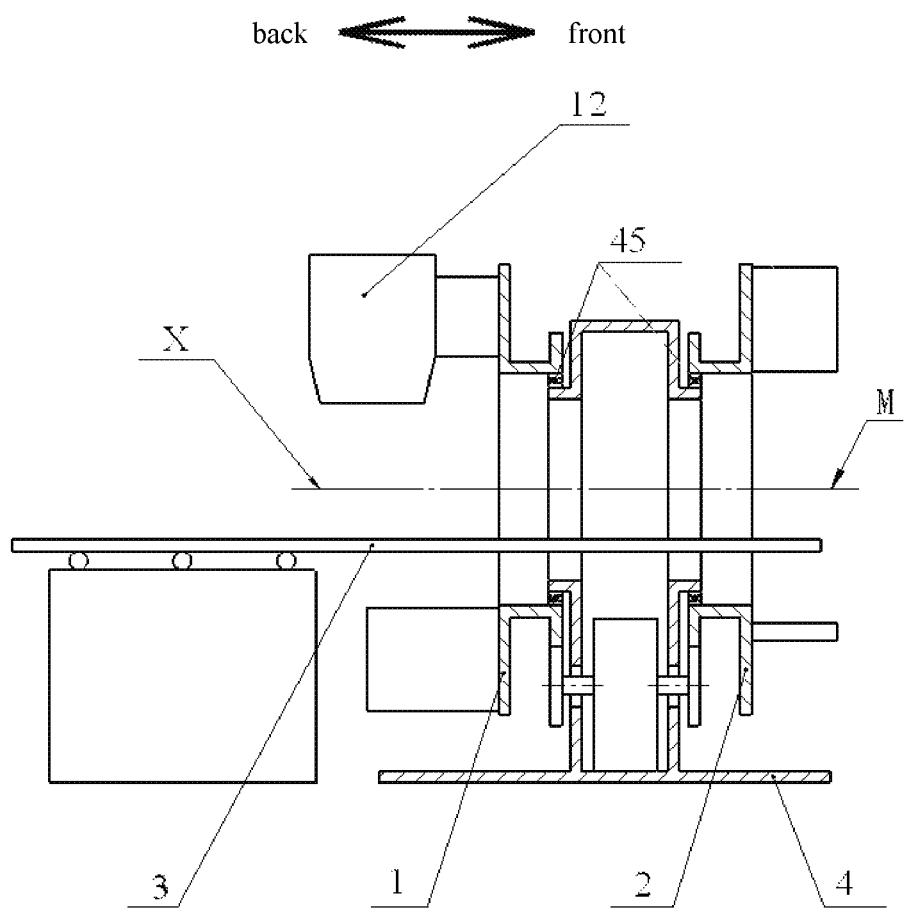
FIG. 9 is a cross-sectional structural schematic drawing of the RT-CT integrated device as shown in FIG. 2 in Embodiment 2.
Figure 10:
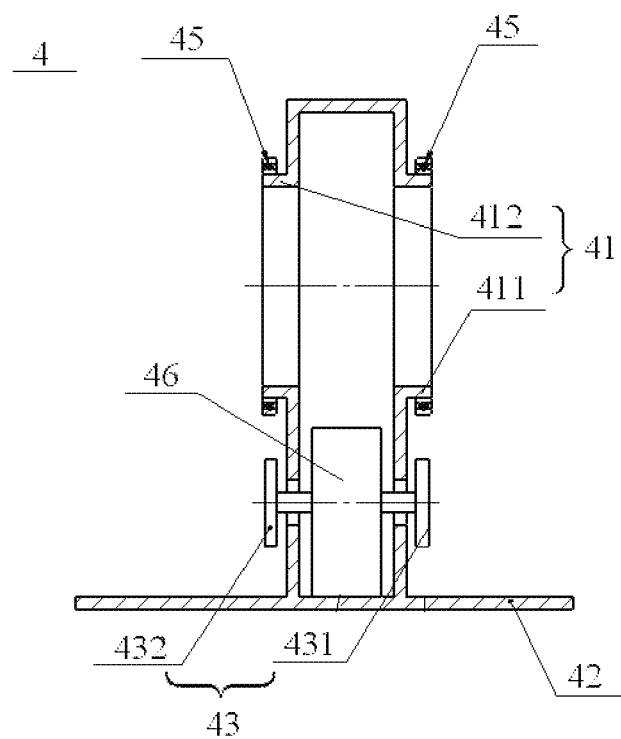
FIG. 10 is a cross-sectional structural schematic drawing of the support system in the RT-CT integrated device as shown in FIG. 9.

As shown in FIGS. 9 to 12, in support base 42 of support system 4, mounting portion 41 may comprise the first mounting portion 411 and the second mounting portion 412. The first mounting portion 411 and the second mounting portion 412 may be set on the front-end and back-end of support base 42 oppositely with coaxial setting. For example, as shown in FIGS. 9 and 10, the CT device rotatable gantry 21 may be socket-jointed on the first mounting portion 411, and the RT device rotatable gantry 11 may be socket-jointed on the second mounting portion 412. In addition, the CT device rotatable gantry 21 may be fixed with the first mounting portion 411 in axial direction as well as in radial direction and rotational connection along circumferential direction; and, the RT device rotatable gantry 11 may be fixed with the second mounting portion 412 in axial direction as well as in radial direction and rotational connection along circumferential direction.

Specifically, a bearing 45 may be set so as to achieve socket-joint between the CT device rotatable gantry 21 and the first mounting portion 411, as well as socket-joint between the RT device rotatable gantry 11 and the second mounting portion 412. The first mounting portion 411 and the second mounting portion 412 may both be set referring to mounting portion 41 in Embodiment 1, and the only difference between the first mounting portion 411 and the second mounting portion 412 is extension direction, wherein one extends forward while the other extends backward. In the present embodiment, as an example, "the first mounting portion 411 extends forward, and the second mounting portion 412 extends backward" is illustrated.

Specifically, the CT device ray emitter 22 and CT device ray receiver 23 may be set on the front-end surface of the CT device rotatable gantry 21; as shown in FIG. 9, the RT device ray emitter 12 may be set on the back-end surface of the RT device rotatable gantry 11. For the opposite setting of CT device 2 and RT device 1, the first mounting portion 411 and the second mounting portion 412 are within the interval between the RT device ray emitter 12 and CT device 2, then at this moment the high energy ray emitted from the RT device ray emitter 12 basically will not transmitted to CT device 2 at this moment, so the shielding system 5 mentioned above may not be set. Under such condition, the RT device ray emitter 12 may be directly set on the RT device rotatable gantry 11 instead of setting above cantilever 13 for connection.

The first mounting portion 411 and the second mounting portion 412 may be set as a structural form which is sagittal symmetry with regard to support base 42, and they may be adjusted as needed. The RT device rotatable gantry 11 and the CT device rotatable gantry 21 may be set as sagittal symmetry or with approximately the same structures.

In the present embodiment, the first mounting portion 411 and the second mounting portion 412 may be set on support base 42 integrated to improve coaxiality of both. Furthermore, the present RT device rotatable gantry 11 and the CT device rotatable gantry 21 may be directly assembled on support 42, and there is no coordination between both of them, thus may improve assembly reliability in axial direction and control precision of coaxiality as well as decrease assembly difficulty.

As shown in FIG. 10, support base 42 of support system 4 may be approximately set as inverted T-type structure. Where, transversal portion of T-type supports on the ground, and two sides of vertical portion are respectively provided with the first mounting portion 411 and the second mounting portion 412 horizontally stretched, achieving assembly of the CT device rotatable gantry 21 and the RT device rotatable gantry 11 respectively.

The first drive part 431 and the second drive part 432 still may be set, and detailed structure may be set referring to Embodiment 1, which will not be mentioned here.

In particular, as there is no direct assembly relationship between CT device 2 and RT device 1 in the present embodiment, brake part 44 may not be set or braking function may be omitted to further simplify the structure of integrated device. Of course, braking function may be integrated on drive part 43 similar to the drive part 43 in Embodiment 1, so as to control movement of CT device 2 and RT device 1 better.

Figure 11:
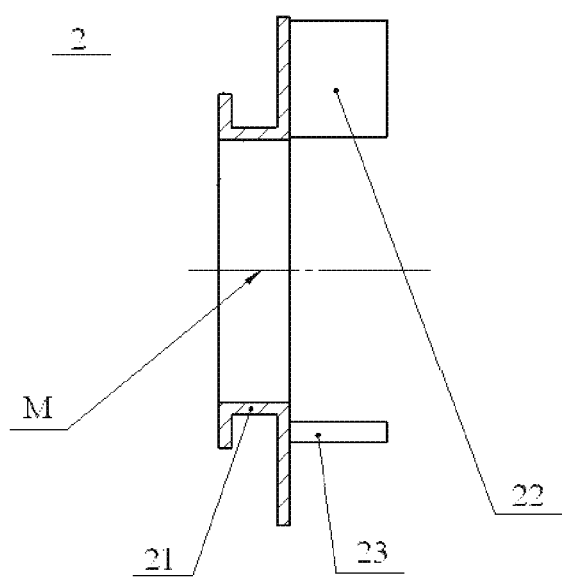
FIG. 11 is a cross-sectional structural schematic drawing of the CT system in the RT-CT integrated device as shown in FIG. 9.

As shown in FIG. 11, the structure of CT device 2 in the present embodiment is approximately the same as that in Embodiment 1, and the CT device rotatable gantry 21 may also be set as hollow columnar structure to form hollow ring-shape rotating disc-type structure; furthermore, the CT device ray emitter 22 and CT device ray receiver 23 may be set on it, and the detailed set-up mode can refer to Embodiment 1. As can be seen from FIG. 11, there is no need to socket-joint RT device 1 on CT device 2 at this moment, then also the second bearing 452 on the CT device rotatable gantry 21. Actually, the only difference between CT device 2 in the present embodiment and that in Embodiment 1 is the direction.

Figure 12:
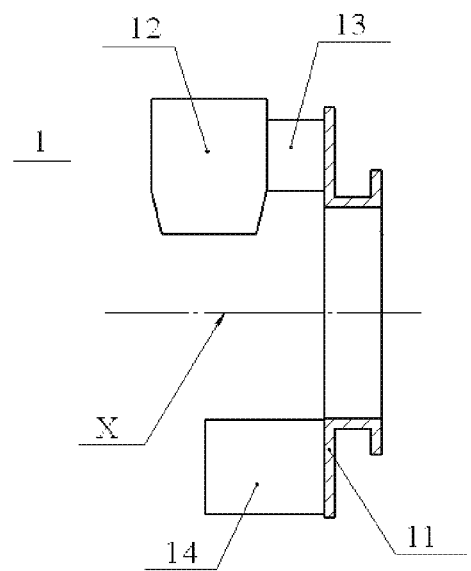
FIG. 12 is a cross-sectional structural schematic drawing of the RT system in the RT-CT integrated device as shown in FIG. 9.

As shown in FIG. 12, RT device 1 in the present embodiment may be set similar to Embodiment 1. Of course, as mentioned above, cantilever 13 of RT device 1 in the present embodiment can be omitted.

Other structures in the present embodiment may all be set referring to Embodiment 1, for example, bearing 45 can be adopted in socket-joint of the first mounting portion 411 and the CT device rotatable gantry 21, socket-joint of the second mounting portion 412 and the RT device rotatable gantry 11, and the axial hole and axle journal coordinated with bearing 45 may be processed through machining to increase coaxiality and to ensure precision of diagnosis and treatment.

Embodiment 3

Figure 13:
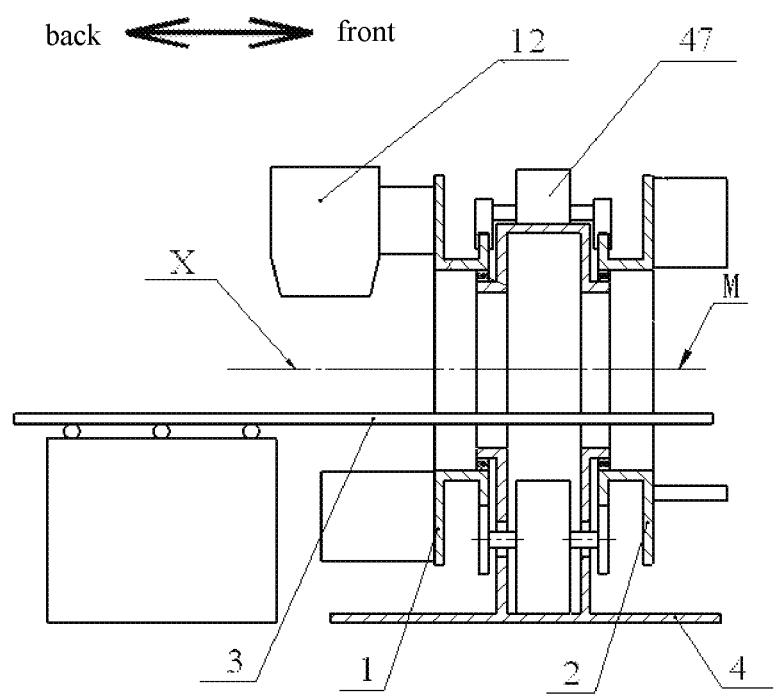
FIG. 13 is a schematic drawing of partial enlargement of the brake part in the RT-CT integrated device as shown in FIG. 2 in Embodiment 3.
Figure 14:
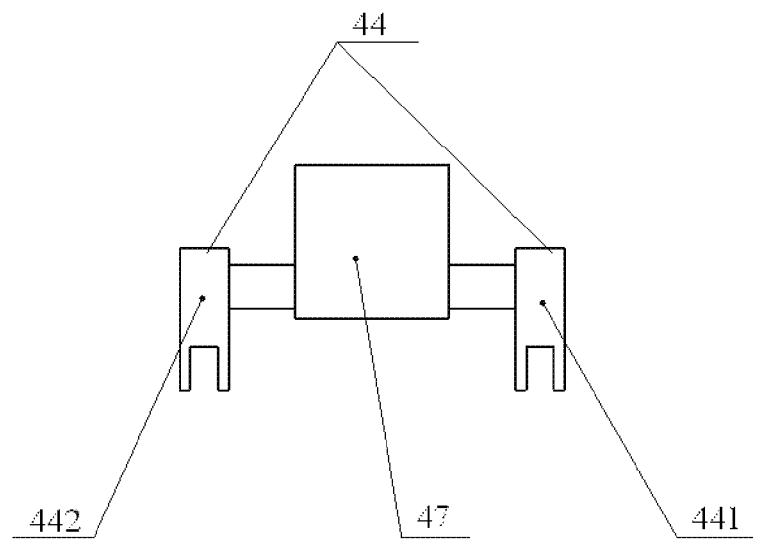
FIG. 14 is a schematic drawing of partial enlargement of the brake part in the RT-CT integrated device as shown in FIG. 13.

As shown in FIGS. 13 and 14, in the embodiment of opposite setting of CT device 2 and RT device 1 in Embodiment 2, a brake part 44 may be set separately.

Specifically, as shown in FIGS. 13 and 14, a support system 4 may also comprise a brake part 44, and the brake part 44 may be set on support base 42 as an independent part for controlling the braking of CT device 2 or RT device 1. It may also be set similar to the brake part 44 in Embodiment 1, and the corresponding brake controlling unit may also be set, which will not be mentioned here, please refer to Embodiment 1.

In particular, as shown in FIG. 14, a brake part 44 may also comprise the first brake part 441 and the second brake part 442 connected with a second bridge base 47 for controlling the braking of the CT device rotatable gantry 21 and rotating 11 of RT device respectively, and both of them may be connected with brake control unit in signal connection.

Detailed scheme of the present embodiment may be set referring to Embodiment 2, or the only difference with Embodiment 2 is brake part 44.

Embodiment 4

As shown in FIG. 15, integrated device of the present application may adopt separated structure.

As shown in FIGS. 16 to 19, RT device 1 in the present embodiment may comprise the RT device rotatable gantry 15, the RT device ray emitter 12 set on the RT device rotatable gantry 15 and RT device drive part 16 used to drive the rotation of RT device rotatable gantry 15. CT device 2 may comprise CT device scanning circle 24 and the CT device rotatable gantry 25. Where, CT device scanning circle 24 is set on the CT device rotatable gantry 25. Under such condition, the CT device rotatable gantry 25 and the RT device rotatable gantry 15 may be configured on the same axis along axial direction and the axial distance of the CT device rotatable gantry 25 and the RT device rotatable gantry 15 may be controlled within predetermined scope. Or, there exists predetermined axial spacing between the CT device rotatable gantry 25 and the RT device rotatable gantry 15. In addition, the first axial through hole 151 extending to CT device scanning circle 24 may be open on the RT device rotatable gantry 15.

Figure 16:
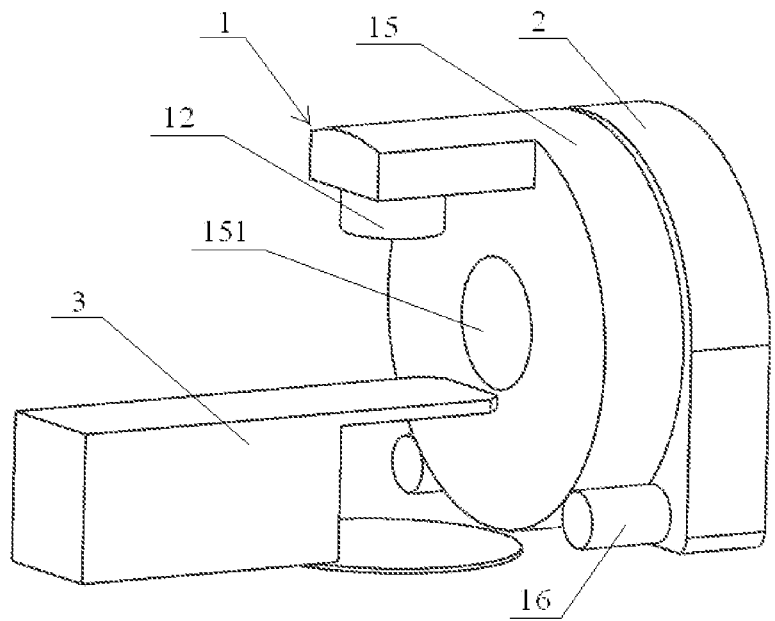
FIG. 16 is an overall structural schematic drawing of the RT-CT integrated device as shown in FIG. 15 in Embodiment 4.

In FIGS. 16 to 19, as an example, "the RT device rotatable gantry 15 in behind, the CT device rotatable gantry 25 in front" is illustrated. As shown in FIG. 16, the RT device rotatable gantry 15 and the CT device rotatable gantry 25 may be relatively independent. Where, the RT device rotatable gantry 15 may be used as the load basis of the RT device ray emitter 12 and for assembling the RT device ray emitter 12. The CT device rotatable gantry 25 may be the load basis of CT device scanning circle 24. For example, CT device scanning circle 24 may be assembled in an interior of CT device rotatable gantry 25, then adjoin the RT device rotatable gantry 15 and the CT device rotatable gantry 25 to arrange both of them on the same end of treatment table 3 in predetermined axial spacing. As the first axial through hole 151 may be open on the RT device rotatable gantry 15, the treatment table 3 may get to CT device scanning circle 24 through the first axial through hole 151 for diagnosis.

Figure 17:
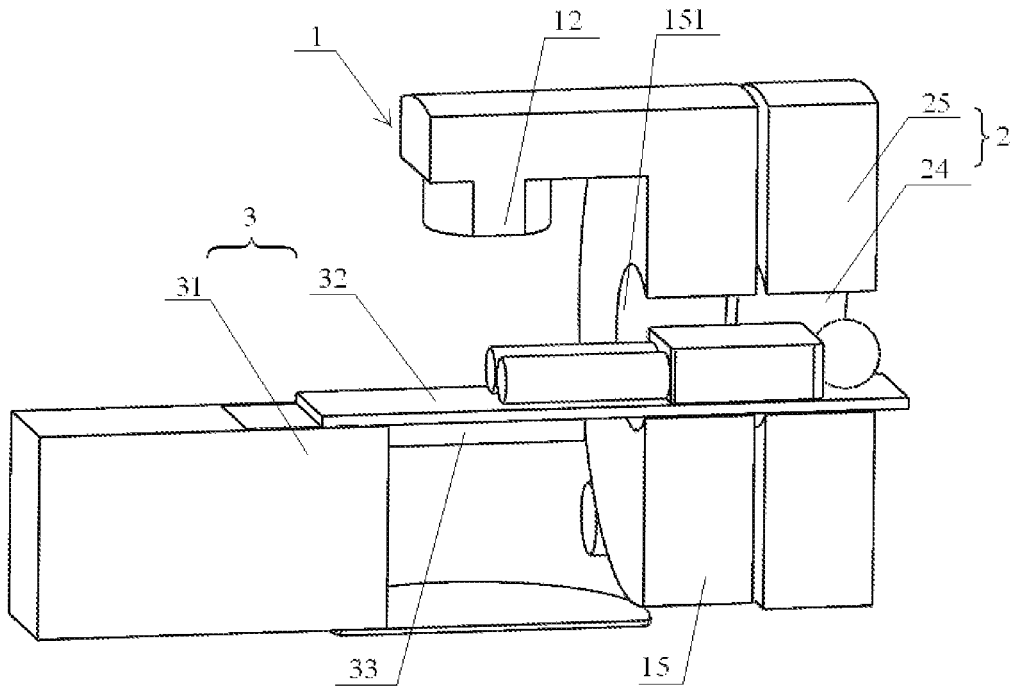
FIG. 17 is a structural schematic drawing of the RT-CT integrated device in the first operating condition as shown in FIG. 16.
Figure 18:
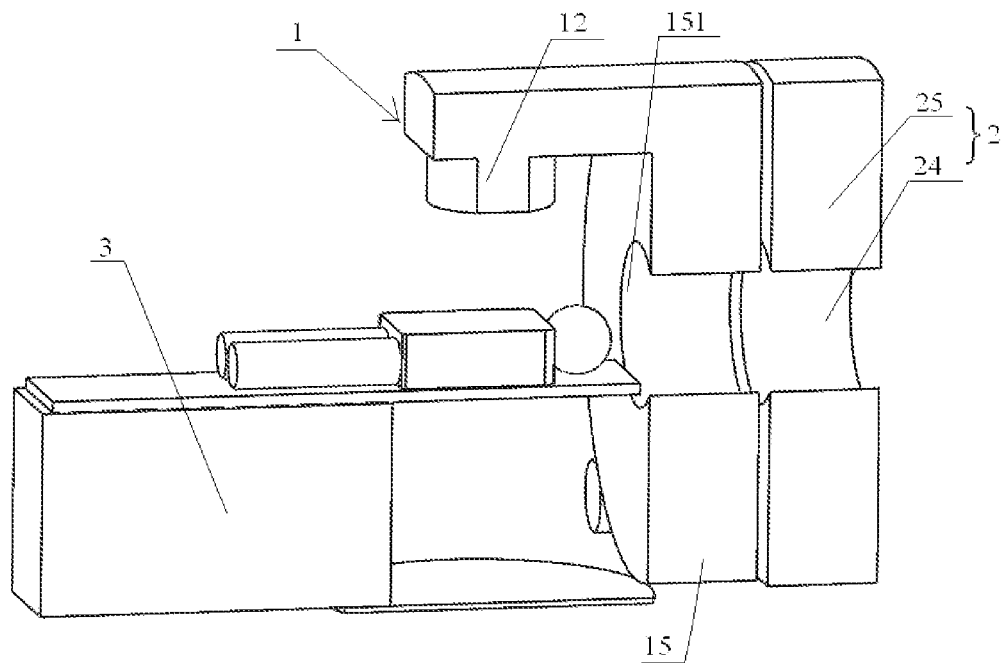
FIG. 18 is a structural schematic drawing of the RT-CT integrated device in the second operating condition as shown in FIG. 16.

As shown in FIG. 17, when diagnosis is needed, treatment table 3 may be driven to shift forward to carry the patient into scanning area of CT device scanning circle 24 for diagnosis on the patient. After the diagnosis, as shown in FIG. 18, treatment table 3 may be driven to shift backward to get to the position corresponding to the RT device ray emitter 12 for radiotherapy.

Specifically, the patient may be fixed on table plate 32 of treatment table 3 using a fixing device, for example, head portion may be fixed with headrest and head mould. Next, table plate 32 is driven to extend forward and extend into inspection hole of CT device scanning circle 24 through the first axial through hole 151 in the middle of the RT device rotatable gantry 15 and runs diagnostic mode. CT device 2 processes scanning and sets lead marking points on the table plate 32, so the positions of tumor and lead marking points may be determined on the CT images when scanning finished, and the deviation between presupposed position of tumor and actual position may be obtained through software calculation. Then, table plate 32 may be driven to shift backward to the treatment position as shown in FIG. 18. At this moment, table plate 32 may correct position of the patient's body referring to the deviation mentioned above, ultimately making the actual position for treatment more accurately for precise treatment.

Both the RT device rotatable gantry 15 and the CT device rotatable gantry 25 may be any well-known structure. Where, the RT device rotatable gantry 15 may be other parts of RT device without related drive structure, for example, the rotatable gantry comprising the RT device ray emitter 12. The CT device rotatable gantry 25 may be main part of CT device, for example, the part only comprises CT device scanning circle 24 may be used as the CT device 2 of the present application.

Figure 19:
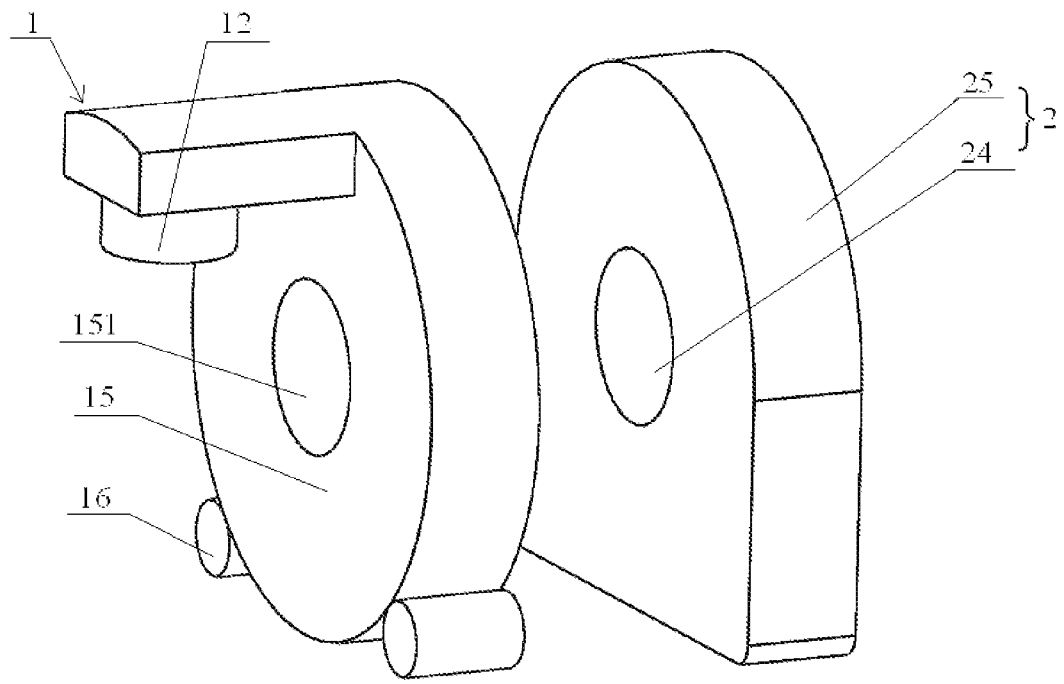
FIG. 19 is an assembly decomposition schematic drawing of the RT-CT integrated device as shown in FIG. 16.

As shown in FIG. 19, the RT device rotatable gantry 15 may be ring-shape drum-type structure. Generally, corresponding drive structure may be assembled in an interior of the RT device rotatable gantry 15. In the present disclosure, to simplify RT device 1 and be convenient for forming the first axial through hole 151, drive structure of the RT device rotatable gantry 15 may be set individually. As shown in FIG. 19, RT device drive part 16 may be set as driving rolls on both sides of the RT device rotatable gantry 15, and driving rolls may be circumscribed with both sides of the RT device rotatable gantry 15. Under such condition, power sources such as electrical machine may be set to drive the rotation of driving rolls, and further obtain the rotation of the RT device rotatable gantry 15.

The structure of the CT device rotatable gantry 25 may be ring-shape structure coordinated with the RT device rotatable gantry 15, and it may be set as other forms, as long as may be used to accommodate CT device scanning circle 24 and to set scanning center-line M and centerline X of radiotherapy in the same coaxial. To be understood, a drive structure to drive the rotation of CT device scanning circle 24 may be set in an interior of the CT device rotatable gantry 25.

In addition, the hole diameter of the first axial through hole 151 on the RT device rotatable gantry 15 may equal to or greater than external diameter of CT device scanning circle 24, so the treatment table 3 may get into CT device scanning circle 24 through the first axial through hole 151. Specifically, the first axial through hole 151 and CT device scanning circle 24 may be set coaxially, and the hole diameter of the first axial through hole 151 may be approximately equal to external diameter of scanning circle 24, at this moment, rotation of the RT device rotatable gantry 15 and rotation of CT device scanning circle 24 may be relatively independent without interference.

The predetermined axial spacing is usually suitable for preventing the collision or contact between the RT device rotatable gantry 15 and the CT device rotatable gantry 25.

To improve coaxiality between the CT device rotatable gantry 25 and the RT device rotatable gantry 15, CT device 2 may also comprise regulation device for adjusting height and angle of inclination of the CT device rotatable gantry 25. Please refer to the prior technologies for the detailed forms of said regulation device, which will not be mentioned here.

Embodiment 5

Figure 20:
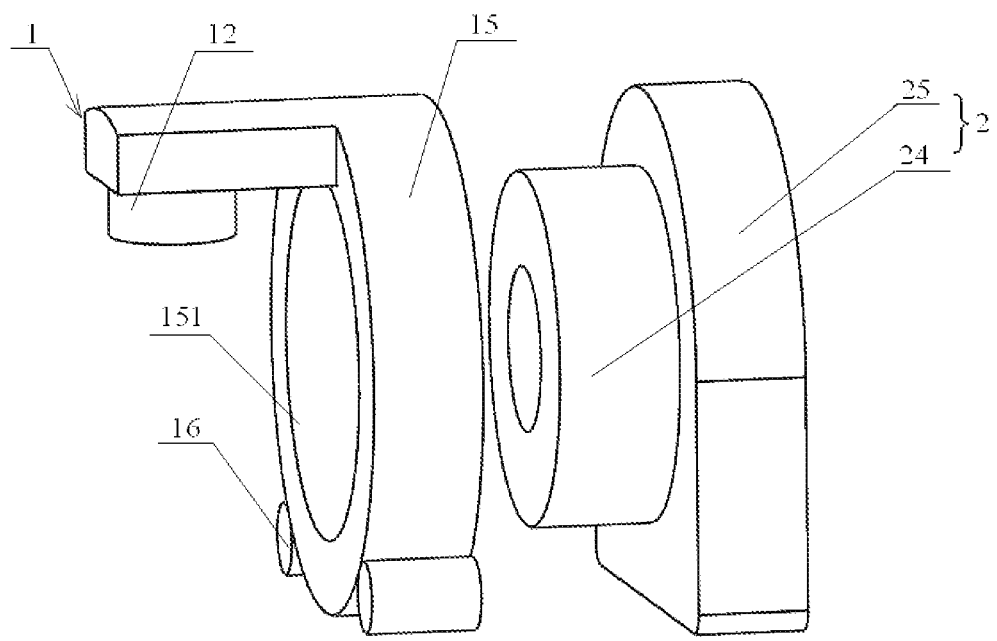
FIG. 20 is an assembly decomposition schematic drawing of the RT-CT integrated device as shown in FIG. 15 in Embodiment 5.
Figure 21:
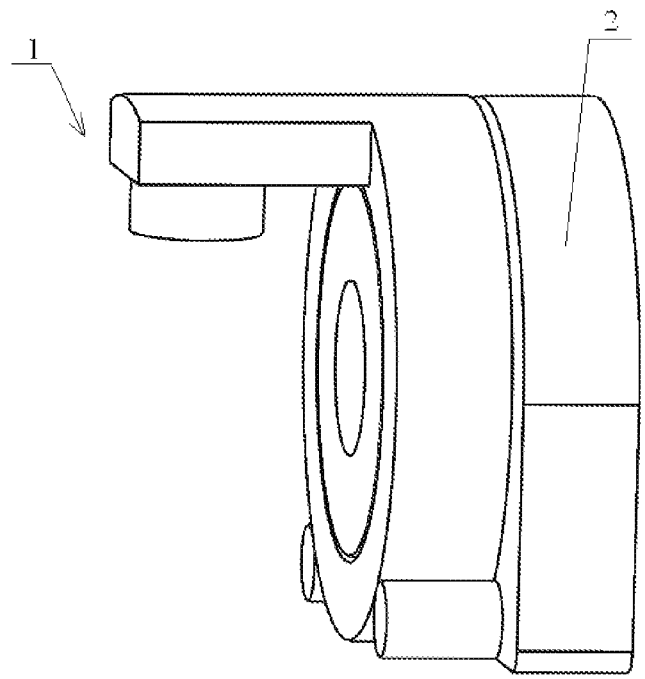
FIG. 21 is a schematic drawing of the RT-CT integrated device as shown in FIG. 20 in combined state.

As shown in FIGS. 20-21, the separated structure shown in Embodiment 5 may be improved to form on the basis of Embodiment 4.

As shown in FIG. 20, CT device scanning circle 24 may be set on an end surface of the CT device rotatable gantry 25. Specifically, it may be set protruding from on an end surface of the CT device rotatable gantry 25 and be stretched in axial direction. In FIG. 20, as an example, "CT device scanning circle 24 is set protruding from back-end surface of the CT device rotatable gantry 25" is illustrated. Under such condition, CT device scanning circle 24 stretches toward the RT device rotatable gantry 15. As shown in FIG. 2, the first axial through hole 151 on the RT device rotatable gantry 15 is sufficient to accommodate CT device scanning circle 24, then CT device scanning circle 24 may stretch into the first axial through hole 151 directly.

At this moment, CT device scanning circle 24 may have a predetermined radial clearance with the first axial through hole 151, to prevent contact or collision with the RT device rotatable gantry 15, and to further ensure reliability of rotation of CT device scanning circle 24.

Meanwhile, RT device rotatable gantry 15 may have a predetermined radial clearance as Embodiment 4 with CT device rotatable gantry 25, to prevent the contact between front-end surface of RT device rotatable gantry 15 and back-end surface of CT device rotatable gantry 25.

The present embodiment and Embodiment 4 only distinguish in that CT device scanning circle 24 is set protruding on an end surface of the CT device rotatable gantry 25, and other parts may be set referring to Embodiment 4.

In addition, the present embodiment may set protective apparatus for shielding ray that may be emitted to CT device scanning circle 24 from the RT device ray emitter 12, and further improving operational reliability and prolonging service life of CT device scanning circle 24.

Embodiment 6

Figure 22:
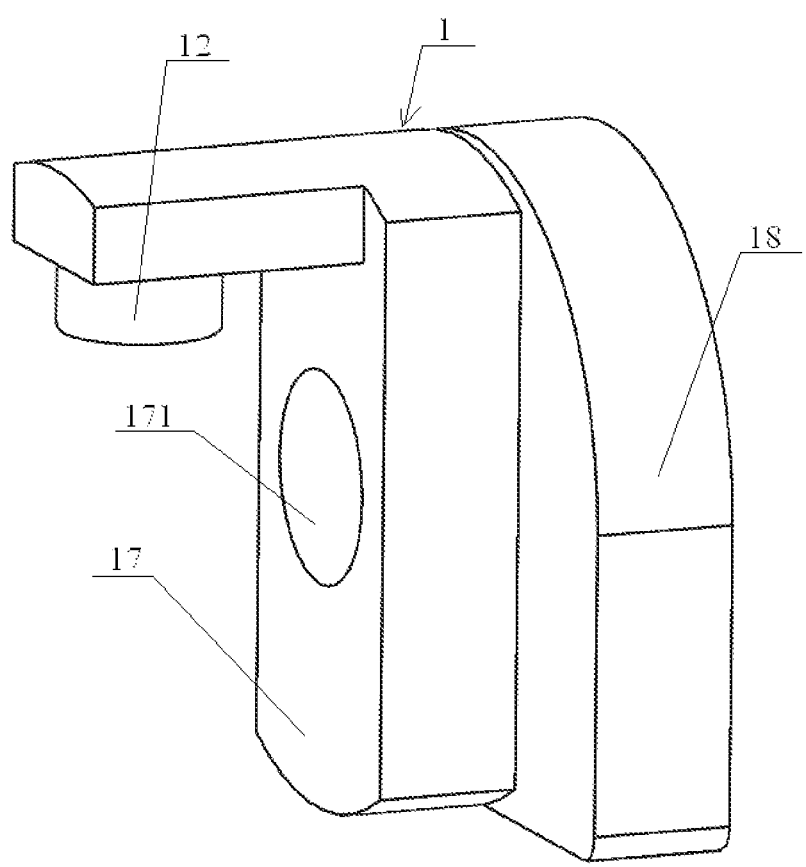
FIG. 22 is a structural schematic drawing of the RT-CT integrated device as shown in FIG. 15 in Embodiment 6.

As shown in FIG. 22, separated structure of integrated device may also be obtained through improvement on RT device.

Specifically, in the present embodiment, RT device 1 may comprise RT device fixing rack 18, the RT device rotatable gantry 17 and the RT device ray emitter 12. Where, the RT device rotatable gantry 17 may be fixed with RT device fixing rack 18 in axial direction as well as in radial direction and rotational connection along circumferential direction. The connection between the RT device rotatable gantry 17 and RT device fixing rack 18 may be obtained through bearing, to obtain the connection mentioned above, and any well-known structure may be used. In addition, the RT device ray emitter 12 may be fixed on said RT device rotatable gantry 17, and please refer to prior technologies for detailed forms.

CT device 2 may comprise CT device scanning circle 24 set in an interior of said RT device fixing rack 18. That is, CT device 2 may only comprise CT device scanning circle 24 for scanning, then provide fixed support through RT device fixing rack 18. Under such condition, the second axial through hole 171 may be open on the RT device rotatable gantry 17 extending to said CT device scanning circle 24, and to form integrated device shown in FIG. 22.

As in RT device fixing rack 18 is set internally with drive structure for driving the rotation of the RT device rotatable gantry 17, there is no need to set drive structure separately for the rotation of the RT device rotatable gantry 17. From appearance, the integrated device in the present embodiment has no difference with single RT device.

Meanwhile, the drive on CT device scanning circle 24 may be obtained through drive structure in RT device fixing rack 18. For example, drive structure in RT device fixing rack 18 may be improved referring to the drive structure of CT device scanning circle 24, or corresponding drive structure of CT device scanning circle 24 may also be set internally in RT device fixing rack 18.

At this moment, the second axial through hole 171 may be set coaxially with CT device scanning circle 24, and its hole diameter may be set as needed, usually not smaller than external diameter of CT device scanning circle 24.

To sum up, the integrated device in the present disclosure, despite integral type or separated structure, both of them have to guarantee coaxial of scanning centerline M and centerline X of radiotherapy. The determining of the coaxial setting may refer to isocenter of RT device. The isocenter refers to, the intersection of rotation axis of treatment head of the RT device ray emitter 12 and rotation axis of rotatable gantry 15 of RT device, which is also the key locating point in treatment process. During treatment, locating accuracy on isocenter mentioned above is required to be less than 1 mm, therefore, accuracy of treatment may be ensured only if locating accuracy on isocenter is ensured.

Advantages of coaxial setting are accurate localization, simple structural design, and may reduce problem of locating accuracy decreasing attributed to multiple moving parts. When CT device 2 and RT device 1 are set coaxially, the locating accuracy may be ensured utmost. Therefore, CT device 2 may rebuild three dimensions model through computed tomography, and may locate positions of internal tumor and locating point on body surface; and location deviation may be calculated through the location of RT device 1 to adjust position of treatment table 3, to ensure location accuracy of treatment and further reduce problems of accumulated error attributed to multiple moving parts.

Adopting integrated device of the present disclosure, diagnosis and treatment may be processed according to the following steps:

Start Treatment→table 3 Moving in→Entering into CT device 2→Performing a scan with CT device 2→Moving into RT device 1→Performing radio therapy through RT device 1→Treatment table 3 moving out→End.

In addition, in the integrated device in the present disclosure, structure of treatment table 3 may be improved correspondingly. Please further refer to FIGS. 17 and 18, treatment table 3 may comprise table body 31 and table plate 32 may be movable connected with said table body 31. A table plate support system 33 may also be set on table body 31, to support table plate 32 when it stretched too long.

Specifically, one of said RT device 1 and said CT device 2 is at a first end away from said treatment table 3, and the other one is at a second end close to said treatment table 3. As shown in FIG. 17, when said table plate 32 stretched into devices at a first end, the table plate support system 33 may support said table plate 32 by stretching said table body 31. As shown in FIG. 18, when table plate 32 is withdrawn back and stretched into device at a second end, the table plate support system 33 may be withdrawn back into table body 31.

The table plate support system 33 may be of various structural forms. Specifically, it may be jackstay or auxiliary support plate; it may be connected to table body 31 in forms of foldable or movable structural form referring to prior technologies, which will not be mentioned here.

To be more specific, there are various detailed forms of integral type and separated structure adopted in integrated device, and the present disclosure only illustrates six of them as examples. But, one skilled in the art can infer more embodiments based on the embodiments mentioned above, and the core of the disclosure is to set RT device 1 and CT device 2 on the same end of treatment table 3, so achievable modes should belong to the protection scope of the present application.

One skilled in the art shall understand that, diagnostic device is not limited to CT device mentioned above, other devices can be adopted to replace CT device in the present application to form new integrated devices. For example, diagnostic devices may be X-ray machine, PET, ECT and other devices; meanwhile, these devices can be improved adopting structures of CT devices mentioned above to integrate with RT device.

The figures are only illustrations of an example, wherein the units or procedure shown in the figures are not necessarily essential for implementing the present disclosure. One skilled in the art will understand that the units in the device in the example can be arranged in the device in the examples as described, or can be alternatively located in one or more devices different from that in the examples. The units in the examples described can be combined into one module or further divided into a plurality of sub-units.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A radiation therapy computed tomography (RT-CT) integrated device comprising a radiation therapy (RT) device and a computed tomography (CT) device, wherein,
 a radiation-therapy centerline of the radiation therapy (RT) device and a scanning centerline of the computed tomography (CT) device are on a same axis,
 the radiation therapy (RT) device and the computed tomography (CT) device are at a same end of a treatment table;
 the radiation therapy (RT) device and the computed tomography (CT) device are integrated onto a support system;
 the support system comprises a support base provided with a mounting portion,
 the computed tomography (CT) device comprises a computed tomography (CT) device rotatable gantry,
 the radiation therapy (RT) device comprises a radiation therapy (RT) device rotatable gantry,
 the computed tomography (CT) device rotatable gantry is provided with a computed tomography (CT) device ray emitter and a computed tomography (CT) device ray receiver,
 the radiation therapy (RT) device rotatable gantry is provided with a radiation therapy (RT) device ray emitter,
 the computed tomography (CT) device rotatable gantry and the radiation therapy (RT) device rotatable gantry are both socket-jointed on the mounting portion, and are disposed coaxially with the mounting portion,
 the computed tomography (CT) device rotatable gantry and the radiation therapy (RT) device rotatable gantry are both fixed in an axial direction and a radial direction;
 the computed tomography (CT) device rotatable gantry and the radiation therapy (RT) device rotatable gantry are both rotatable along a circumferential direction;
 the radiation therapy (RT) device rotatable gantry, the computed tomography (CTS) device rotatable gantry and the mounting portion are socket-jointed sequentially in the axial direction,
 each socket-joint for connecting the radiation therapy (RT) device rotatable gantry, the computed tomography (CT) device rotatable gantry and the mounting portion sequentially is fixed in the axial direction and the radial direction; and
 each socket-joint for connecting the radiation therapy (RT) device rotatable gantry, the computed tomography (CT) device rotatable gantry and the mounting portion sequentially is rotatable along the circumferential direction.

2. The radiation therapy-computed tomography (RT-CT) integrated device according to claim 1, wherein
 the computed tomography (CT) device ray emitter and the computed tomography (CT) device ray receiver are located at two radial sides of the computed tomography (CT) device rotatable gantry respectively, and the computed tomography (CT) device ray emitter and the computed tomography (CT) device ray receiver are set on an end of the computed tomography (CT) device rotatable gantry at which the computed tomography (CT) device rotatable gantry is socket-jointed to the radiation therapy (RT) device rotatable gantry, the radiation therapy (RT) device ray emitter is set at an end of the radiation therapy (RT) device rotatable gantry away from the computed tomography (CT) device rotatable gantry.

3. The radiation therapy-computed tomography (RT-CT) integrated device according to claim 2, wherein the radiation therapy (RT) device further comprises a cantilever, the cantilever extends towards a direction away from the computed tomography (CT) device rotatable gantry with its root portion connected to the radiation therapy (RT) device rotatable gantry, the radiation therapy (RT) device ray emitter is set at a head portion of the cantilever.

4. The radiation therapy-computed tomography (RT-CT) integrated device according to claim 3, further comprising a shielding system, the shielding system is used to shield the computed tomography (CT) device ray receiver against rays emitted from the radiation therapy (RT) device ray emitter.

5. The radiation therapy-computed tomography (RT-CT) integrated device according to claim 1, wherein, the mounting portion comprises a first mounting portion and a second mounting portion which are disposed coaxially and oppositely, the computed tomography (CT) device rotatable gantry is socket-jointed to the first mounting portion, wherein the first mounting portion is fixed in the axial direction and the radial direction, and the second mounting portion is rotational along the circumferential direction;

the radiation therapy (RT) device rotatable gantry is socket-jointed to the second mounting portion, wherein the second mounting portion is fixed in the axial direction and the radial direction, and the second mounting portion is rotational along the circumferential direction.

6. The radiation therapy-computed tomography (RT-CT) integrated device according to claim 5, wherein the radiation therapy (RT) device further comprises a counterweight, the counterweight and the radiation therapy (RT) device ray emitter are located in different semi-circumference of the radiation therapy (RT) device rotatable gantry.

7. The radiation therapy-computed tomography (RT-CT) integrated device according to claim 1, wherein the support system further comprises a drive part, the drive part is used to drive at least one of the radiation therapy (RT) device rotatable gantry and the computed tomography (CT) device rotatable gantry to rotate along the circumferential direction.

8. The radiation therapy-computed tomography (RT-CT) integrated device according to claim 7, wherein the drive part comprising:

a first drive part driving the computed tomography (CT) device rotatable gantry to rotate along the circumferential direction, and a second drive part driving the radiation therapy (RT) device rotatable gantry to rotate along the circumferential direction.

9. The radiation therapy-computed tomography (RT-CT) integrated device according to claim 7, wherein the support system further comprises a brake part, the brake part is used to brake at least one of the radiation therapy (RT) device rotatable gantry and the computed tomography (CT) device rotatable gantry.

10. The radiation therapy-computed tomography (RT-CT) integrated device according to claim 9, wherein the brake part comprises:

a first brake part for braking the computed tomography (CT) device rotatable gantry, and a second brake part for braking the radiation therapy (RT) device rotatable gantry.

11. The radiation therapy-computed tomography (RT-CT) integrated device according to claim 1, wherein, the treatment table comprises a table body and a movable table plate connected to the table body, the table body is further provided with a table plate support system;

one of the radiation therapy (RT) device and the computed tomography (CT) device is located at a first end away from the treatment table, and the other is located at a second end close to the treatment table;

when the movable table plate stretches into the radiation therapy (RT) device or the computed tomography (CT) device at the first end, the table plate support system extends out from the table body to support the movable table plate.

12. A radiation therapy-computed tomography (RT-CT) integrated device comprising a radiation therapy (RT) device and a computed tomography (CT) device, wherein, a radiation-therapy centerline of the radiation therapy (RT) device and a scanning centerline of the computed tomography (CT) device are on a same axis, the radiation therapy (RT) device and the computed tomography (CT) device are at a same end of a treatment table;

the radiation therapy (RT) device and the computed tomography (CT) device are integrated onto a support system;

the radiation therapy (RT) device and the computed tomography (CT) device are independent from each other;

the radiation therapy (RT) device comprises a radiation therapy (RT) device rotatable gantry, a radiation therapy (RT) device ray emitter set on the radiation therapy (RT) device rotatable gantry and a RT device drive part for driving the radiation therapy (RT) device rotatable gantry to rotate;

the computed tomography (CT) device comprises a computed tomography (CT) device rotatable gantry having a computed tomography (CT) device scanning circle, wherein a diagnosis is performed within a scanning area of the computed tomography (CT) device scanning circle;

the computed tomography (CT) device rotatable gantry and the radiation therapy (RT) device rotatable gantry are arranged along a same axis with a predetermined axial spacing, and the radiation therapy (RT) device rotatable gantry is provided with a first axial through hole extending to the computed tomography (CT) device scanning circle;

the computed tomography (CT) device scanning circle protrudes from an end surface of the computed tomography (CT) device rotatable gantry and stretches into the first axial through hole;

further comprising a radial spacing between the computed tomography (CT) device scanning circle and the first axial through hole.

13. The radiation therapy-computed tomography (RT-CT) integrated device according to claim 12, further comprising a protective apparatus shielding the computed tomography (CT) device scanning circle against rays emitted from the radiation therapy (RT) device ray emitter.

14. The radiation therapy-computed tomography (RT-CT) integrated device according to claim 12, wherein the computed tomography (CT) device further comprises an adjustment apparatus adjusting height and inclination of the computed tomography (CT) device rotatable gantry.

15. The radiation therapy-computed tomography (RT-CT) integrated device according to claim 12, wherein,
- the treatment table comprises a table body and a movable table plate connected to the table body,
- the table body is further provided with a table plate support system;
- one of the radiation therapy (RT) device and the computed tomography (CT) device is located at a first end away from the treatment table, and the other is located at a second end close to the treatment table;
- when the movable table plate stretches into the radiation therapy (RT) device or the computed tomography (CT) device at the first end, the table plate support system extends out from the table body to support the movable table plate.

16. The radiation therapy-computed tomography (RT-CT) integrated device according to claim 12, wherein,
- the radiation therapy (RT) device drive part is driving rolls set on and circumscribed with both sides of the radiation therapy (RT) device rotatable gantry.

* * * * *